US008526627B2

(12) United States Patent
Asao et al.

(10) Patent No.: US 8,526,627 B2

(45) Date of Patent: Sep. 3, 2013

(54) NOISE REDUCTION DEVICE

(75) Inventors: Yoshifumi Asao, Osaka (JP); Tsuyoshi Maeda, Hyogo (JP)

(73) Assignee: Panasonic Corporation, Osaka (JP)

( * ) Notice: Subject to any disclaimer, the term of this patent is extended or adjusted under 35 U.S.C. 154(b) by 336 days.

(21) Appl. No.: 13/042,497

(22) Filed: Mar. 8, 2011

(65) Prior Publication Data

US 2011/0222698 A1 Sep. 15, 2011

(30) Foreign Application Priority Data

Mar. 12, 2010 (JP) ................................. 2010-055714

(51) Int. Cl.

*A61F 11/06* (2006.01)
*G10K 11/16* (2006.01)
*H03B 29/00* (2006.01)

(52) U.S. Cl.

USPC ....... 381/71.1; 381/71.2; 381/71.4; 381/71.8; 381/73.1; 381/94.1; 704/226; 704/227; 704/228

(58) Field of Classification Search

USPC .................. 381/71.1, 71.2, 71.4, 71.8, 71.11, 381/71.12, 73.1, 94.1, 94.7, 56–59; 704/226, 704/227, 228; 379/392.01; 348/231.4, 423.1, 348/207.99

See application file for complete search history.

(56) References Cited

U.S. PATENT DOCUMENTS

| | | | | |
|---|---|---|---|---|
| 6,041,126 | A | 3/2000 | Terai et al. | |
| 6,343,127 | B1 * | 1/2002 | Billoud | 381/71.4 |
| 2009/0260916 | A1 | 10/2009 | Kassner | |
| 2010/0027804 | A1 | 2/2010 | Kano | |

FOREIGN PATENT DOCUMENTS

| | | | |
|---|---|---|---|
| JP | 02-285799 | A | 11/1990 |
| JP | 09-36784 | A | 2/1997 |
| JP | 09-146559 | A | 6/1997 |
| JP | 10-247088 | A | 9/1998 |
| JP | 2007-047367 | A | 2/2007 |
| JP | 2009-257326 | A | 11/2009 |
| WO | 2009/084186 | A1 | 7/2009 |

OTHER PUBLICATIONS

Full translation of JP 09-146559 A previously cited in the Information Disclosure Statement dated Mar. 8, 2011.

* cited by examiner

*Primary Examiner* — Vivian Chin
*Assistant Examiner* — Paul Kim
(74) *Attorney, Agent, or Firm* — Pearne & Gordon LLP

(57) ABSTRACT

A noise reduction device of the present invention comprises a control filter unit for generating a control sound signal to cancel out a noise, a control speaker for outputting a control sound according to the control sound signal from the control filter unit, an error microphone for detecting a residual sound by superimposing the noise upon the control sound output from the control speaker, and an obstacle detector for detecting an obstacle around the error microphone, wherein the control filter unit generates the control sound signal according to data from the error microphone and the obstacle detector.

9 Claims, 9 Drawing Sheets

FIG. 6

| | Pattern 1 | Pattern 2 | Pattern 3 | Pattern 4 | Pattern 5 | Pattern 6 | Pattern 7 | Pattern 8 |
|---|---|---|---|---|---|---|---|---|
| Noise detecting microphone 11 (R_Mic11) | O | O | O | O | × | × | × | × |
| Noise detecting microphone 12 (R_Mic12) | O | O | × | × | O | O | × | × |
| Noise detecting microphone 13 (R_Mic13) | O | × | O | × | O | × | O | × |
| Fixed filter 21 | $F_{11}$ | $F_{21}$ | $F_{31}$ | $F_{41}$ | — | — | — | — |
| Fixed filter 22 | $F_{12}$ | $F_{22}$ | — | — | $F_{52}$ | $F_{62}$ | — | — |
| Fixed filter 23 | $F_{13}$ | — | $F_{33}$ | — | $F_{53}$ | — | $F_{73}$ | — |

O: No obstacle ×: Obstacle $F_{11}$, $F_{12}$, $F_{13}$, ···· $F_{73}$: Filter coefficient

NOISE REDUCTION DEVICE

TECHNICAL FIELD

The present invention relates to a noise reduction device and, in particular, it relates to a noise reduction device capable of actively reducing noise coming to a control point.

BACKGROUND ART

When providing information such as voice guidance and the like services to passengers sitting in seats inside an aircraft, a railcar and the like filled with loud noise, the noise in the seats becomes a problem.

An interior space confined within a continuous wall like that of an aircraft or a car has a kind of sealed structure, and the noise environment remains persistent for the passengers when there is a noise source either inside or outside the space. Depending on a level of the noise, it can become a factor of physical and mental stresses to the passengers, and it therefore impairs the comfort. The noise thus poses a serious problem in the quality of service especially when the service is provided for the passengers inside a cabin in an aircraft and the like.

In the case of an aircraft, the noise of apparatuses such as propellers and engines for generating thrust of the aircraft and the sound associated with airflow produced around the airframe moving in the aerial space such as a wind noise during the flight are main sources of the noise. Since the noise inside the cabin interferes with the voice guidance and the like services in addition to causing discomfort of the passengers, an improvement of it is strongly desired.

To this end, the methods hitherto used are passive damping means in most instances, such that a sound insulation material having sound absorbing properties like sound barrier material and acoustic absorbing material is disposed between the sealed structure and the noise source as the measures to reduce the noise inside the sealed cabin. A high-density barrier material and a sound-absorbing sheet are examples used as the sound barrier material and the acoustic absorbing material respectively. Any material of sound absorbing property generally has a high density, which accompanies an extra weight. The fuel consumption increases with increase in weight, and the cruising range decreases. It hence causes a decline in economical efficiency and deterioration of the function as an aircraft. There are also other aspects of functionality such as decrease in the strength as being susceptible to damages and the design of esthetical quality that are not ignorable as the structural materials.

To address the problems associated with the noise reduction measures using the passive damping means discussed above, there exists an idea disclosed recently of a noise reduction device capable of executing control for reduction of noise coming to a control point by selectively operating any of a fixed filter and an adaptive filter and outputting a control sound of opposite phase to that of the noise coming to the control point (known as active noise control, refer to Patent Literature 1, for example).

In this example, the noise reduction device comprises noise-detecting microphone 9101, adaptive filter 9201, control speaker 9401, error microphone 9501 and fixed filter 9601, as shown in FIG. 9, and the device executes the noise control by selecting adaptive filter 9201 when a change occurs in the condition of noise. Noise-detecting microphone 9101 detects a noise and outputs it as a noise signal to adaptive filter 9201. Adaptive filter 9201 executes signal processing on the noise signal by using a filter coefficient and generates a control signal, and control speaker 9401 outputs a control sound toward the control point. Error microphone 9501 is placed in the control point for detecting a difference between the noise and the control sound, and output it as an error signal. Adaptive filter 9201 executes an updating process of the filter coefficient in a manner to minimize the error signal by using the Filtered-X_LMS algorism, for instance, to update the filter coefficient in response to a change in the condition of the noise, and generates a new control signal. When the filter coefficient being updated converges, the device carries out the noise control by selecting fixed filter 9601, which is preset with the converged filter coefficient.

The above method may make the noise-detecting microphone and the error microphone unable to continue their normal detecting functions if there is any obstacle such as a pillow, blanket, book and the like object placed around the microphones, thereby leaving a problem of presenting a possibility of increasing the noise in the control point depending on a condition of such obstacle. Among some measures known to address this problem, there are techniques disclosed as conventional arts, one of which optimizes the control by changing the filter coefficient according to a distance to the obstacle if any, and the other suppresses an abnormal sound attributed to the obstacle by setting a threshold for the filter coefficient (refer to Patent Literatures 2 and 3, for example).

According to the above conventional arts, however, the devices are designed to calculate the filter coefficient continuously in real time, and hence there has remained a possibility depending on the condition of the obstacle that the noise becomes larger than that without carrying out the control for noise reduction, and it discomforts the passengers when a control sound updated according to the calculated filter coefficient is output immediately. Moreover, the above arts have not given any consideration to operation with the noise-detecting microphone covered with an obstacle, thereby making it unlikely to achieve a steady effect of the noise reduction.

CITATION LIST

Patent Literatures

Patent Literature 1: Unexamined Japanese Patent Publication No. H02-285799

Patent Literature 2: Unexamined Japanese Patent Publication No. H09-146559

Patent Literature 3: Unexamined Japanese Patent Publication No. 2007-047367

DISCLOSURE OF INVENTION

A noise reduction device of the present invention comprises a noise controller unit for generating a control sound signal to cancel out a noise, a control sound output unit for outputting a control sound according to the control sound signal from the noise controller unit, a residual sound detector for detecting a residual sound by superimposing the control sound on the noise, and an obstacle detector for detecting an obstacle in the vicinity of the residual sound detector, wherein the noise controller unit generates the control sound signal according to data from the residual sound detector and the obstacle detector.

By virtue of the above structure, it becomes possible to execute control of the noise reduction including such cases that obstacles exist, thereby providing the noise reduction device capable of executing the control steadily with high quality even in an environment where the obstacles exist.

Furthermore, the noise reduction device of the present invention comprises a noise detector for detecting a noise supplied from at least one noise source, a noise controller unit for generating a control sound signal to cancel out the noise detected by the noise detector, a control sound output unit for outputting a control sound according to the control sound signal from the noise controller unit, a residual sound detector for detecting a residual sound by superimposing the control sound on the noise supplied from the noise source, and an obstacle detector for detecting an obstacle to at least one of the noise detector and the residual sound detector, wherein the noise controller unit generates the control sound signal according to data from the noise detector, the residual sound detector and the obstacle detector.

It becomes possible by virtue of the above structure to detect the noise and execute control of noise reduction including such cases that obstacles exist. Thus provided is the noise reduction device capable of executing even steadier and higher quality of control under the environment where the obstacles exist.

BRIEF DESCRIPTION OF DRAWINGS

FIG. 6 is a control table used for generating the control sound of the noise reduction device according to the first exemplary embodiment of the invention;

DETAILED DESCRIPTION OF PREFERRED EMBODIMENTS

Description is provided first of the fundamental concept of the present invention with reference to FIGS. 1A, 1B, 1C and 2, before detailing an exemplary embodiment of the invention.

Figure 1A:
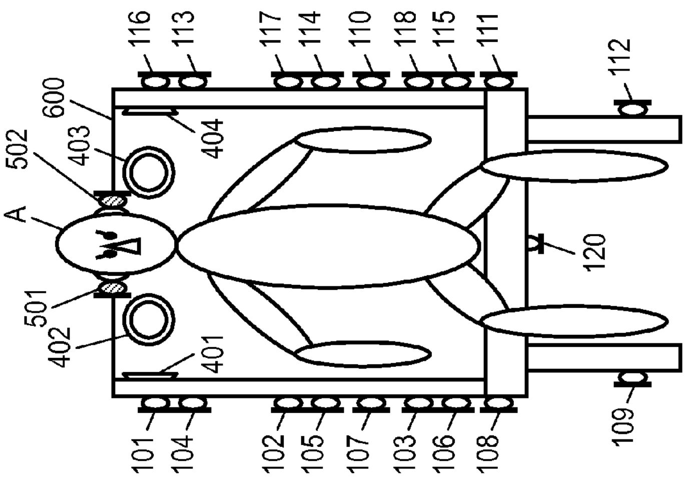
FIG. 1A is a front view of a noise reduction device showing an example of mounted configuration according to a first exemplary embodiment of the present invention.
Figure 1B:
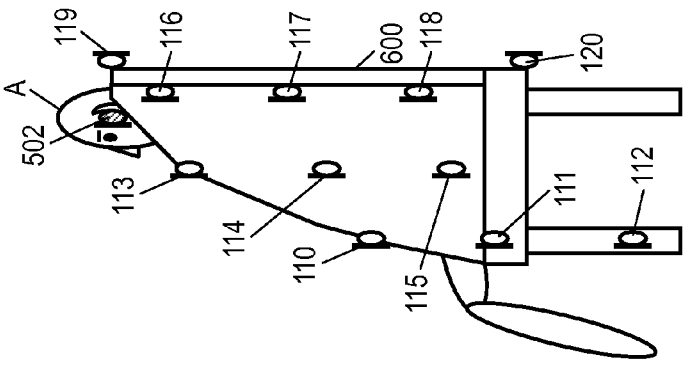
FIG. 1B is a side view of the noise reduction device showing the example of mounted configuration according to the first exemplary embodiment of the invention.
Figure 1C:
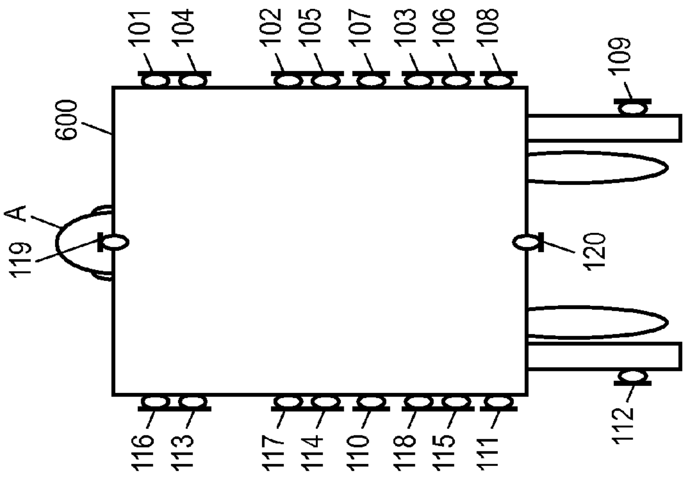
FIG. 1C is a rear view of the noise reduction device showing the example of mounted configuration according to the first exemplary embodiment of the invention.
Figure 2:
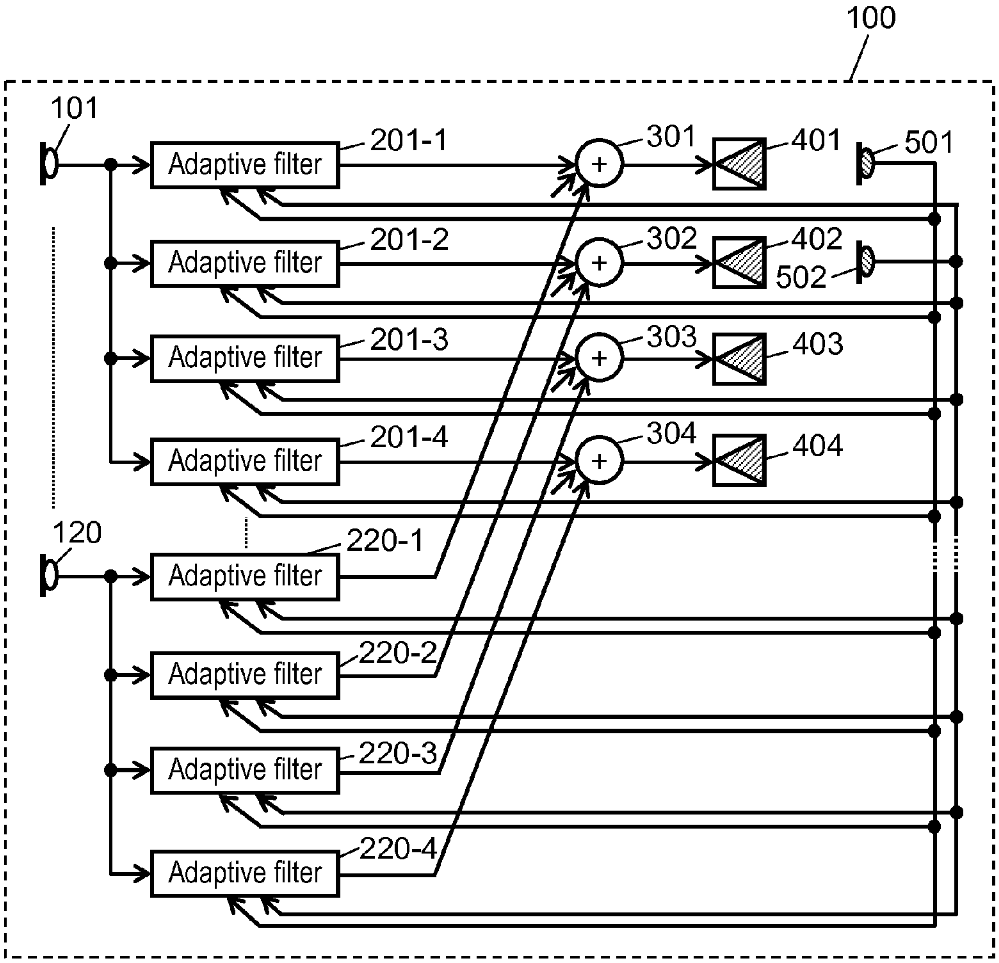
FIG. 2 is a block diagram showing a basic circuit structure of the noise reduction device according to the first exemplary embodiment of the invention.

FIG. 1A is a front view showing an example of seat 600 of an aircraft with passenger (i.e., a user) A sitting therein, and FIGS. 1B and 1C are a side view and rear view respectively. FIG. 2 is a block diagram showing a circuit structure of a noise reduction device mounted to seat 600 shown in FIGS. 1A to 1C.

As illustrated in FIGS. 1A to 1C, noise-detecting microphones 101 to 120 are disposed to exterior sides of seat 600. Control speakers 401 to 404 are disposed to inner surfaces of seat 600 at positions of equal height to the ears of user A. Control points are set to be at the ears of user A, and error microphones 501 and 502 are placed on the ears of user A designated as the control points, as one example.

Noise reduction device 100 comprises noise-detecting microphones 101 to 120, adaptive filters 201-1 to 220-1, 201-2 to 220-2, 201-3 to 220-3 and 201-4 to 220-4, adders 301 to 304, control speakers 401 to 404, and error microphones 501 and 502, as shown in FIG. 2.

A noise detected by noise-detecting microphone 101 is output as a noise signal to adaptive filters 201-1 to 201-4. Another noise detected by noise-detecting microphone 102 is output as another noise signal to adaptive filters 202-1 to 202-4. In the same manner as above, noises detected by noise-detecting microphones 103 to 120 are output to their corresponding adaptive filters 203 to 220 having suffixes "-1" to "-4" respectively.

Adaptive filter 201-1 includes a transfer function necessary from control speaker 401 to error microphone 501 and another transfer function necessary from control speaker 401 to error microphone 502, which are preset in advance by using the Filtered-X_LMS algorism. Adaptive filter 201-1 updates a filter coefficient thereof in a manner to minimize individual error signals from error microphones 501 and 502 collectively by using the individually preset transfer functions.

Error microphones 501 and 502 are placed in the control points, so that they detects the noise coming to these control points from a noise source and control sound coming to these control points from control speakers 401 to 404. The incoming noise and the control sound from control speakers 401 to 404 reaching these control points interfere with one another (or, superimposed) in each of error microphones 501 and 502, and a difference between the noise and the control sound is hence detected as an error signal (i.e., residual sound signal).

Likewise, adaptive filter 202-1 includes a preset transfer function from control speaker 401 to error microphone 501 and another transfer function from control speaker 401 to error microphone 502. Adaptive filter 202-1 updates its filter coefficient in a manner to minimize individual error signals from error microphones 501 and 502 collectively by using the individually preset transfer functions.

In the same manner as above, each of other adaptive filters 203-1 to 220-1 also includes a preset transfer function from control speaker 401 to error microphone 501 and another transfer function from control speaker 401 to error microphone 502. Adaptive filters 203-1 to 220-1 update their respective filter coefficients to minimize individual error signals from error microphones 501 and 502 collectively by using the individually preset transfer functions.

Similarly, each of adaptive filters 201-2 to 220-2 includes a preset transfer function from control speaker 402 to error microphone 501 and another transfer function from control speaker 402 to error microphone 502. Adaptive filters 201-2 to 220-2 update their respective filter coefficients to minimize individual error signals from error microphones 501 and 502 collectively by using the individually preset transfer functions.

Likewise, each of adaptive filters 201-3 to 220-3 includes a preset transfer function from control speaker 403 to error microphone 501 and another transfer function from control speaker 403 to error microphone 502. Adaptive filters 201-3 to 220-3 update their respective filter coefficients to minimize individual error signals from error microphones 501 and 502 collectively by using the individually preset transfer functions.

Moreover, each of adaptive filters 201-4 to 220-4 includes a preset transfer function from control speaker 404 to error microphone 501 and another transfer function from control speaker 404 to error microphone 502. Adaptive filters 201-4 to 220-4 update their respective filter coefficients to minimize individual error signals from error microphones 501 and 502 collectively by using the individually preset transfer functions.

Adaptive filters 201-1 to 220-1 execute signal processing on the noise signals input therein by using the updated filter coefficients, and the respective results are output as control signals to adder 301. Adder 301 adds up the control signals from adaptive filters 201-1 to 220-1, and outputs the result to control speaker 401. Control speaker 401 outputs a control sound according to the control signal from adder 301 toward error microphones 501 and 502 at the control points.

Adaptive filters 201-2 to 220-2 execute signal processing on the noise signals input therein by using the updated filter coefficients, and the respective results are output as control signals to adder 302. Adder 302 adds up the control signals from adaptive filters 201-2 to 220-2 and outputs the result to control speaker 402. Control speaker 402 outputs a control sound according to the control signal from adder 302 toward error microphones 501 and 502 at the control points.

Adaptive filters 201-3 to 220-3 execute signal processing on the noise signals input therein by using the updated filter coefficients, and the respective results are output as control signals to adder 303. Adder 303 adds up the control signals from adaptive filters 201-3 to 220-3 and outputs the result to control speaker 403. Control speaker 403 outputs a control sound according to the control signal from adder 303 toward error microphones 501 and 502 at the control points.

Adaptive filters 201-4 to 220-4 execute signal processing on the noise signals input therein by using the updated filter coefficients, and the respective results are output as control signals to adder 304. Adder 304 adds up the control signals from adaptive filters 201-4 to 220-4 and outputs the result to control speaker 404. Control speaker 404 outputs a control sound according to the control signal from adder 304 toward error microphones 501 and 502 at the control points.

Accordingly, noise reduction device 100 mounted to seat 600 can reduce the incoming noise to the ears of user A, i.e., the control points, by virtue of the updating process of the filter coefficients discussed above.

In this example, it becomes possible even when noise control is carried out only with fixed filters to demonstrate the effect of noise reduction equivalent to the case, in which the noise control is done with the adaptive filters if there are practically no changes in at least one of frequency and level of the noise, or the changes remain within a certain range of variations.

However, this does not necessarily mean that an optimum filter coefficient can always be prepared in advance for use as a filter coefficient set to each fixed filter since the noise varies in type depending on position of the seat. It is also difficult to ensure the preset filter coefficient to remain optimum for an extended period of time even if it is initially the optimum filter coefficient, because of changes in the installation environment due to renewal of equipments, age deterioration and the like.

In the case of an aircraft having a large numbers of seats, for instance, it becomes necessary to work with the individual seats in order to obtain an optimum filter coefficient for each of them. Furthermore, the task of obtaining the optimum filter coefficient for each seat becomes enormous since airframe, engines, configuration of seats, etc. vary from one model to another, besides certain cases that different air carriers use different engines.

The present invention addresses the problems discussed above, and makes possible full use of the optimum effect of noise reduction at all times by updating the filter coefficient according to a position of the seat and surrounding environment from the value set to the fixed filter when the noise is comparatively stable. In addition, the invention can substantially reduce man-hours necessary to set the filter coefficient for each seat by enabling the updating task of filter coefficient automatically.

Description will be provided hereinafter of an exemplary embodiment of the present invention with reference to the drawings.

Exemplary Embodiment

Figure 3C:
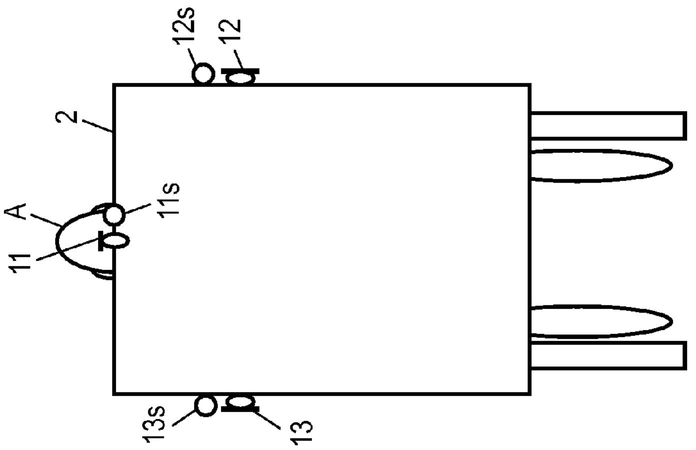
FIG. 3C is a rear view showing the main component layout to illustrate the operation of the noise reduction device according to the first exemplary embodiment of the invention.
Figure 3B:
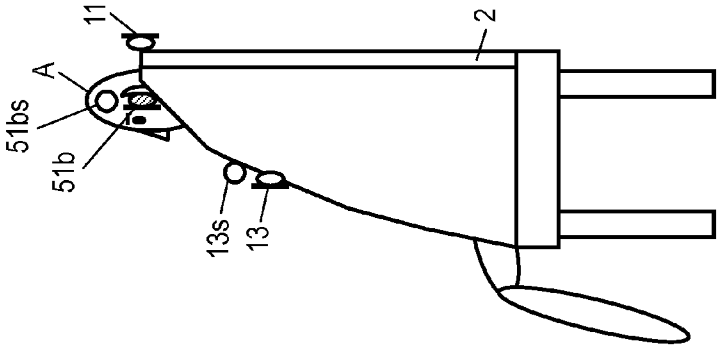
FIG. 3B is a side view showing the main component layout to illustrate the operation of the noise reduction device according to the first exemplary embodiment of the invention.
Figure 3A:
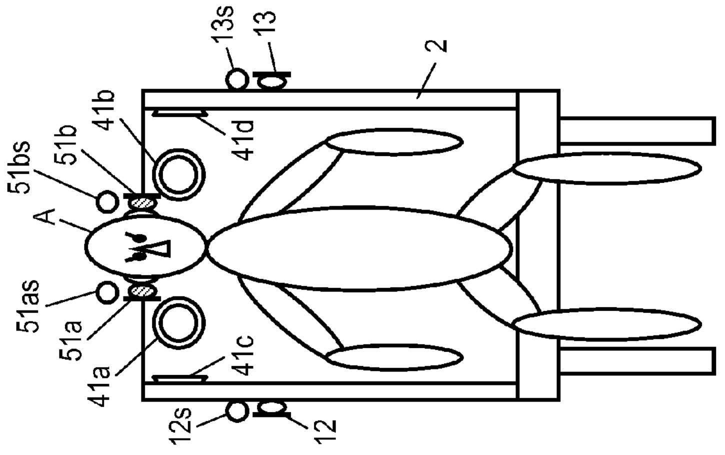
FIG. 3A is a front view showing a main component layout to illustrate operation of the noise reduction device according to the first exemplary embodiment of the invention.
Figure 4:
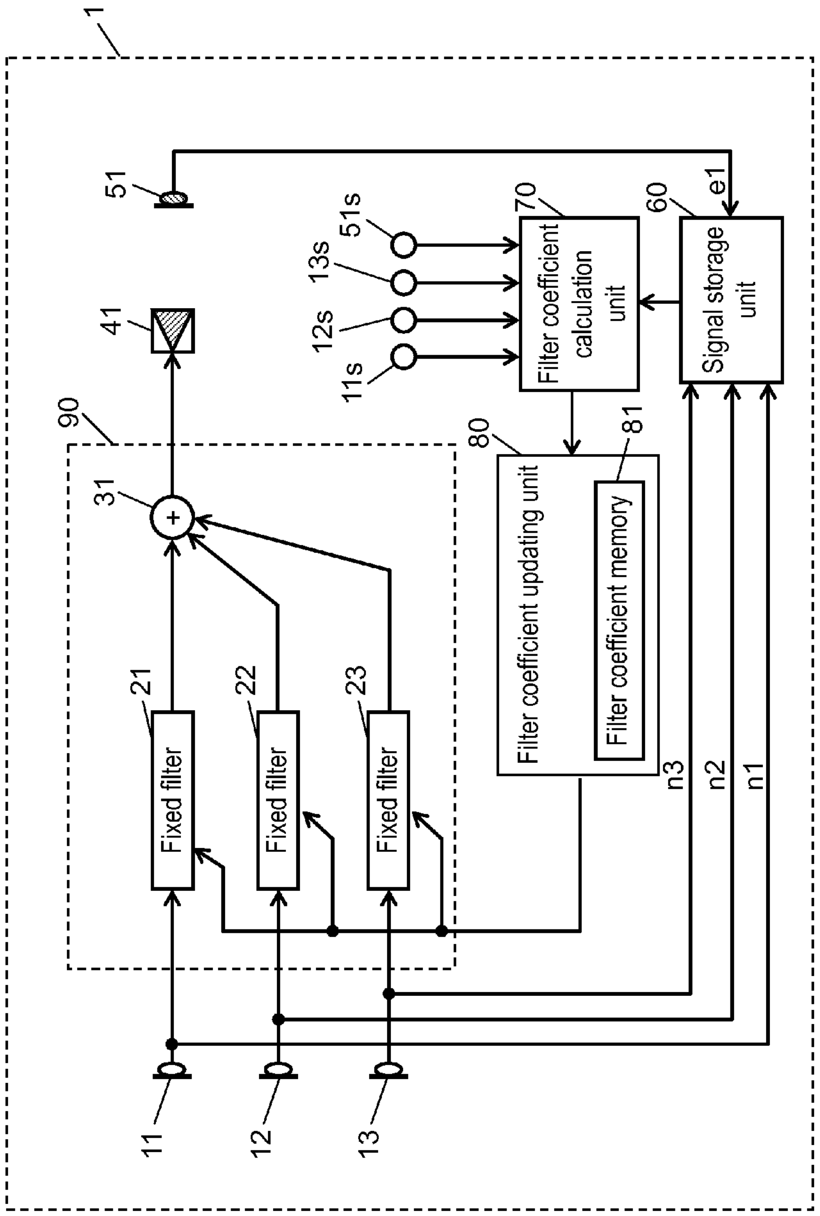
FIG. 4 is a block diagram showing a main structure involved in generation of a control sound of the noise reduction device according to the first exemplary embodiment of the invention.

Referring now to FIG. 3A to FIG. 5, description is provided of a circuit structure and operation related to updating of filter coefficients, which is the primary feature of noise reduction device 1 (hereinafter referred to simply as device 1) according to the first exemplary embodiment of the present invention. FIG. 3A is a front view showing an example of seat 2 of an aircraft with user A sitting therein, and FIGS. 3B and 3C are a side view and a rear view respectively. FIG. 4 is a block diagram showing a circuit structure of device 1 mounted to seat 2.

In the example shown in FIG. 1A to FIG. 2, noise reduction device 100 has been illustrated as having twenty (20) noise-detecting microphones. However, device 1 being presented here is an example having three (3) noise-detecting microphones in order to simplify the following explanation. In any instance where a number of the noise-detecting microphones is increased or decreased, it will become obvious that advantages of the present invention can be demonstrated effectively by either expanding or simplifying the structure based on the concept discussed below.

As shown in FIGS. 3A to 3C, device 1 comprises three noise-detecting microphones 11 to 13 disposed to exterior sides of seat 2 to serve as noise detectors for detecting noises for the control purpose, and they output the detected incoming noises as control sound signals to control filter unit 90. There are four control speakers 41*a* to 41*d* disposed to inner surfaces of seat 2 at positions of equal height to the ears of user A. Control points are set to be at the ears of user A. Control speakers 41*a* to 41*d* (these speakers 41*a* to 41*d* are collectively referred to hereinafter as speaker 41) receive a control signal generated in control filter unit 90, and output control sounds simultaneously toward the control points. Error microphones 51*a* and 51*b* (these error microphones 51*a* and 51*b* are collectively referred to hereinafter as error microphone 51) are placed in positions of seat 2 close to ears of user A when seated, for example.

As shown next in FIG. 4, device 1 comprises noise-detecting microphones 11 to 13 serving as the noise detectors, control filter unit 90, control speaker 41 representing a control sound output unit, signal storage unit 60, filter coefficient calculation unit 70, filter coefficient updating unit 80 and error microphone 51 serving as a residual sound detector. Here, control filter unit 90, signal storage unit 60, filter coefficient calculation unit 70 and filter coefficient updating unit 80 compose a noise controller unit.

Control filter unit 90 and control speaker 41 operate in a manner as described hereinafter.

Control filter unit 90 is provided with fixed filters 21 to 23 and adder 31. A noise detected by noise-detecting microphone 11 is output as a control sound signal to fixed filter 21. Likewise, noises detected by noise-detecting microphones 12 and 13 are output as control sound signals to fixed filters 22 and 23 respectively.

Fixed filter 21 executes signal processing on the control sound signal from noise-detecting microphone 11 by using a fixed filter coefficient set by filter coefficient calculation unit 70 and filter coefficient updating unit 80, as will be described later, and outputs it as a control signal to adder 31. The filter coefficient set to fixed filter 21 is a coefficient obtained for the purpose that the control sound output from control speaker 41 according to the generated control signal becomes opposite in phase at the control point with respect to a phase of a predetermined noise that reaches the same control point.

The predetermined noise means a noise generated inside an aircraft while flying at a normal cruising speed, and the filter coefficient set to each of fixed filters 21 to 23 shall be the one calculated when at least one of frequency and level of the predetermined noise reaching the control point is varying within a certain range of variations.

Similarly, fixed filters 22 and 23 execute signal processing on the control sound signal from noise-detecting microphones 12 and 13 by using fixed filter coefficients set respectively by filter coefficient calculation unit 70 and filter coefficient updating unit 80, as will be described later, and output control signals to adder 31. The filter coefficients set to fixed filters 22 and 23 also have the same characteristics as the filter coefficient of fixed filter 21.

Adder 31 adds up the control signals received from fixed filters 21 to 23, and outputs the result to control speaker 41. Control speaker 41 outputs a control sound according to the control signal from adder 31 toward the control point.

Error microphone 51 detects the noise at the mounted position. Error microphone 51 used as a residual sound detector is disposed in the control point, and detects the noise coming from a noise source and the control sound coming from control speakers 41 at the control point. The incoming noise and the control sound reaching the control point interfere with each other (or, superimposed) in error microphone 51, and a difference is detected as an error signal (i.e., residual sound signal).

Signal storage unit 60 records noise signals n1 to n3 from noise-detecting microphones 11 to 13 and error signal e1 from error microphone 51 for a predetermined period of time into an internal memory or the like, for instance. Upon completion of the recording, signal storage unit 60 gives filter coefficient calculation unit 70 a command of starting calculation of filter coefficients.

In response to the command from signal storage unit 60, filter coefficient calculation unit 70 calculates filter coefficients of fixed filters 21 to 23 provided inside control filter unit 90 by using data recorded in signal storage unit 60.

Filter coefficient updating unit 80 reads the filter coefficients calculated by filter coefficient calculation unit 70 at a predetermined timing, and renews the filter coefficients set to fixed filters 21 to 23 with the filter coefficients read from the filter coefficient calculation unit 70.

Figure 5:
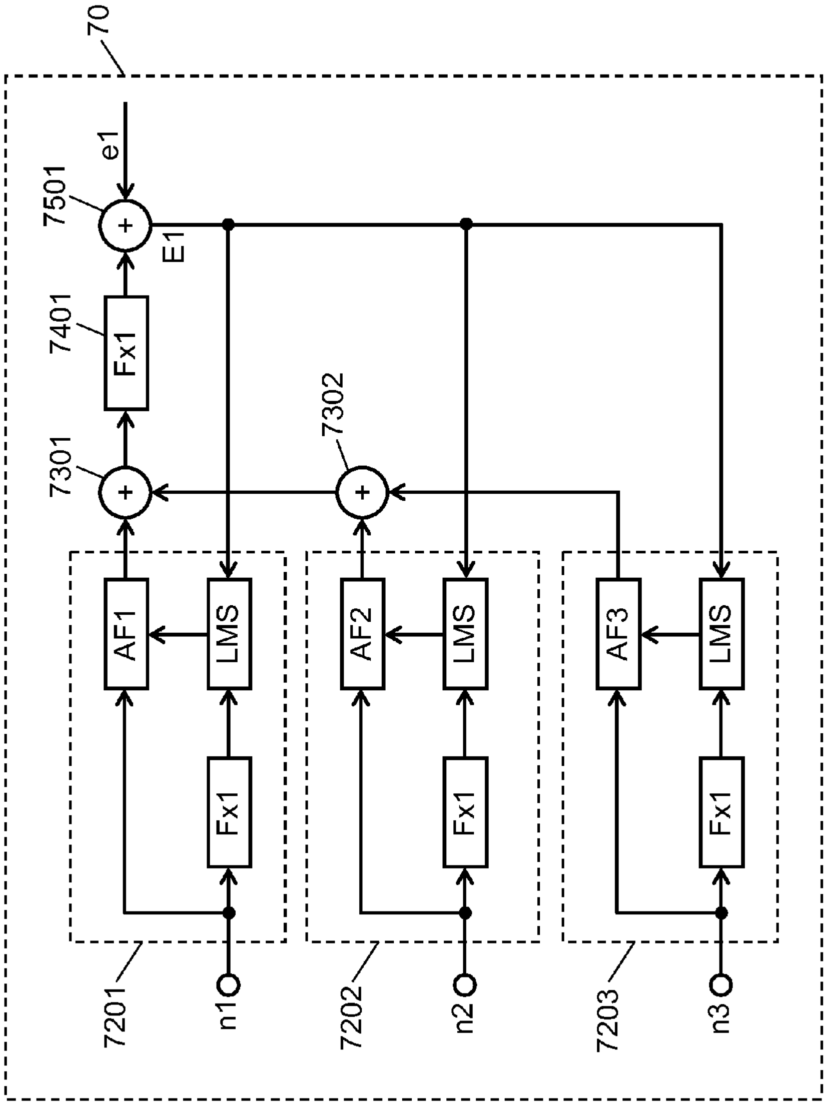
FIG. 5 is another block diagram showing a detailed structure involved in generation of the control sound of the noise reduction device according to the first exemplary embodiment of the invention.

Description is provided next of a structure of filter coefficient calculation unit 70 and how it operates by using FIG. 5. FIG. 5 is a block diagram showing an example of circuit structure of filter coefficient calculation unit 70.

Filter coefficient calculation unit 70 comprises adaptive filters 7201 to 7203, adders 7301 and 7302, acoustic system filter 7401 and adder 7501.

Noise signals n1 to n3 received from signal storage unit 60 are input to adaptive filters 7201 to 7203.

Adaptive filters 7201 to 7203 include a transfer function (Fx1) necessary from control speaker 41 to error microphone 51, which is preset in advance by using the Filtered-X_LMS algorism.

Adaptive filters 7201 to 7203 execute signal processing on the noise signals n1 to n3 respectively input therein by using the preset filter coefficient, and the results are output as control signals to adders 7301 and 7302. Adder 7301 adds up the control signals from adaptive filters 7201 to 7203 in the end, and outputs the result to acoustic system filter 7401.

Acoustic system filter 7401 has a transfer function (Fx1) from control speaker 41 to error microphone 51, which is preset in advance, and the control signal having passed through acoustic system filter 7401 is output to adder 7501. Adder 7501 also receives an input of error signal e1 so that adder 7501 adds up these input signals.

The added signal output from adder 7501 is input as error signal E1 into adaptive filters 7201 to 7203, which in turn update their respective filter coefficients in a manner to minimize error signal E1.

As discussed above, noise signals n1 to n3 and error signal e1 are recorded as the data in a predetermined time period (one minute, for instance), and filter coefficient calculation unit 70 has access to this data for repeated use until filter coefficients of adaptive filters 7201 to 7203 finally converge.

Since filter coefficient calculation unit 70 is constructed independently from control filter unit 90 that outputs the control sound via control speaker 41, it can carry out the process without dependent on a processing speed of control filter unit 90. Although control filter unit 90 is required to execute its process in real time to complete the process within a predetermined sampling period, filter coefficient calculation unit 70 needs not complete its process within the sampling period in real time. It is therefore free to set a series of processing time for filter coefficient calculation unit 70 relative to real time, so that a time to calculate (or converge) the filter coefficients can be shortened when the process is arranged to complete faster. For example, filter coefficient calculation unit 70 can complete the calculation quicker than that of real time by making its processing operation faster than the sampling period. On the other hand, an operating load and an amount of the operation per unit time of filter coefficient calculation unit 70 can be reduced by making its series of processing time slower than that of real time. In this case, the coefficients calculated by filter coefficient calculation unit 70 come to be same as the coefficients obtained on the basis of the sampling period even though the processing time is longer than that of real time since noise signals n1 to n3 and error signal e1 are the signals sampled in real time.

Filter coefficient calculation unit 70 calculates the filter coefficients effective to reduce the noise coming to the control points by the updating process of the filter coefficients described above.

When the filter coefficients for use to update those in adaptive filters 7201 to 7203 converge, filter coefficient updating unit 80 (in FIG. 4) updates the filter coefficients set to fixed filters 21 to 23 in control filter unit 90 to the converged filter coefficients at a predetermined timing.

The update timing may be determined in any manner, for instance, by using the same timing as the filter coefficients converge in adaptive filters 7201 to 7203, or to update at such intervals as once every few minutes or even several days. Or, it may be appropriate to carry out the update at a timing of the first flight of the aircraft, and at subsequent timing whenever furnishings and the like equipment inside the aircraft are renewed.

When update of the filter coefficients in adaptive filters 7201 to 7203 converge, filter coefficient calculation unit 70 gives to signal storage unit 60 a command of recording the noise signal, the error signal and the filter coefficients in the individual adaptive filters at the time of convergence, designated as data of convergence. Subsequently, filter coefficient calculation unit 70 carries out a process of allocating the filter coefficients as being fixed filter coefficients to AF1, AF2 and AF3 of adaptive filters 7201 to 7203 by using the data of convergence stored in signal storage unit 60, and inputs through acoustic system filter 7401 each of the noise signal and the error signal at the time of convergence to adder 7501 wherein they are added up. It may be appropriate to so configure the structure that the coefficients in fixed filters 21 to 23 in control filter unit 90 are updated to the calculated coefficients in filter coefficient updating unit 80 when the output from adder 7501 is within a range of predetermined values.

It is thus possible by virtue of this structure to prevent control speaker 41 from outputting an inappropriate control sound to cause discomfort to the user even if an extra time is needed for filter coefficient calculation unit 70 to calculate the filter coefficients and a condition of the noise changes in the mean time.

As discussed above, this device 1 calculates the optimum filter coefficients independently in filter coefficient calculation unit 70 irrespective of the real time operation of control filter unit 90, and it is hence capable of having filter coefficient updating unit 80 update the filter coefficients preset to fixed filters 21 to 23 at the predetermined timing.

It can hence provide a full advantage of reducing a throughput related to calculation of the filter coefficients besides the ability of calculating the optimum filter coefficients according to position of the seat and surrounding environment.

In addition, the calculated filter coefficients are not applied immediately to fixed filters 21 to 23, which avoid updating to improper filter coefficients. Accordingly, even when a trouble occurs due to an obstacle, etc. in which the filter coefficients diverge, there is never an output of any control sound resulting from the diverged filter coefficients, so as to prevent discomfort to the user.

As a result, device 1 can exert the optimum effect of noise reduction at all times by way of changing the filter coefficients preset to fixed filters 21 to 23 to the optimum filter coefficients according to the position of the seat and the surrounding environment.

Referring next to FIG. 6 to FIG. 8B, description is provided of a structure and operation to cope with an influence exerted upon noise-detecting microphones 11 to 13 and error microphone 51 due to any obstacle, which is the second feature of device 1.

First, device 1 has a structure to cope with obstacles, comprising obstacle detectors 11*s* to 13*s*, 51*as* and 51*bs* (obstacle detectors 51*as* and 51*bs* are collectively referred to as obstacle detector 51*s*), located individually in the vicinity of each of three noise-detecting microphones 11 to 13 and two error microphones 51*a* and 51*b*, such that each of the obstacle detectors is disposed next to every microphone as shown in FIGS. 3A to 3C. The obstacle detectors may be disposed in any such manner as one each of the microphones and the obstacle detectors are mounted to a seat separately but close to each other, a microphone and an obstacle detector are integrated by embedding the obstacle detector in the microphone, a pair of microphone and obstacle detector are united and mounted to the seat as a single unit, or the like. With regard to mounting locations of the obstacle detectors, consideration is made first to identify probable obstacles that may affect detecting function of the microphones, and determination is made for locations of the obstacle detectors in relation to the microphones based on assumption of possible conditions of the identified obstacles, so as to help improve detecting effect of the obstacle detectors. Presence or absence of obstacles can be determined by a method of, for instance, generating a signal sound from control speaker 41 and finding any change in the acoustic characteristic of the signal detected by error microphone 51. The same method is also effective for making the determination with other noise-detecting microphones 11 to 13. In this case, the determination of obstacles can be made without giving nuisance to the user by utilizing an inaudible signal such as an ultrasonic signal. When such a signal sound is used, the above-mentioned obstacle detectors 11*s* to 13*s* and 51*s* become unnecessary. It is also possible to use a pressure sensor, infrared sensor, gravimetric sensor, camera and the like as the obstacle detector besides the one using signal sound.

Figure 8A:
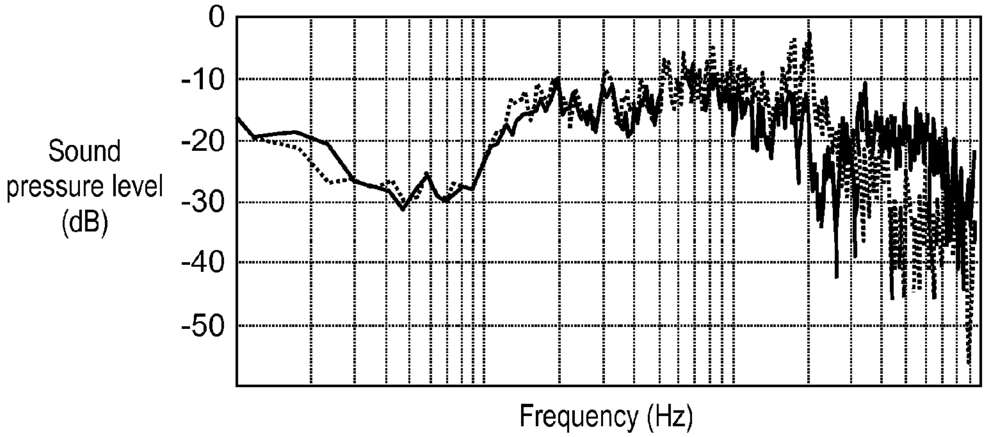
FIG. 8A is a graphic representation showing frequency characteristic of white noise produced from a control speaker and detected by an error microphone of the noise reduction device according to the first exemplary embodiment of the invention.
Figure 8B:
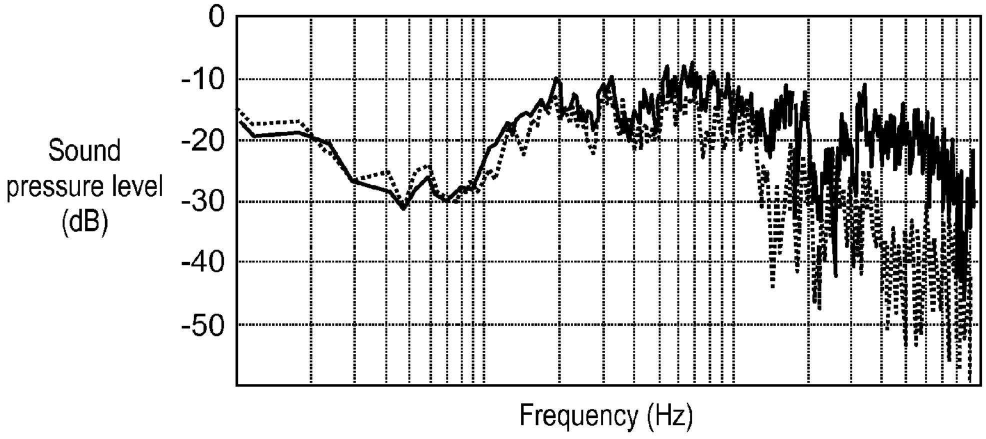
FIG. 8B is another graphic representation showing frequency characteristic of white noise produced from the control speaker and detected by the error microphone of the noise reduction device according to the first exemplary embodiment of the invention.
Figure 9:
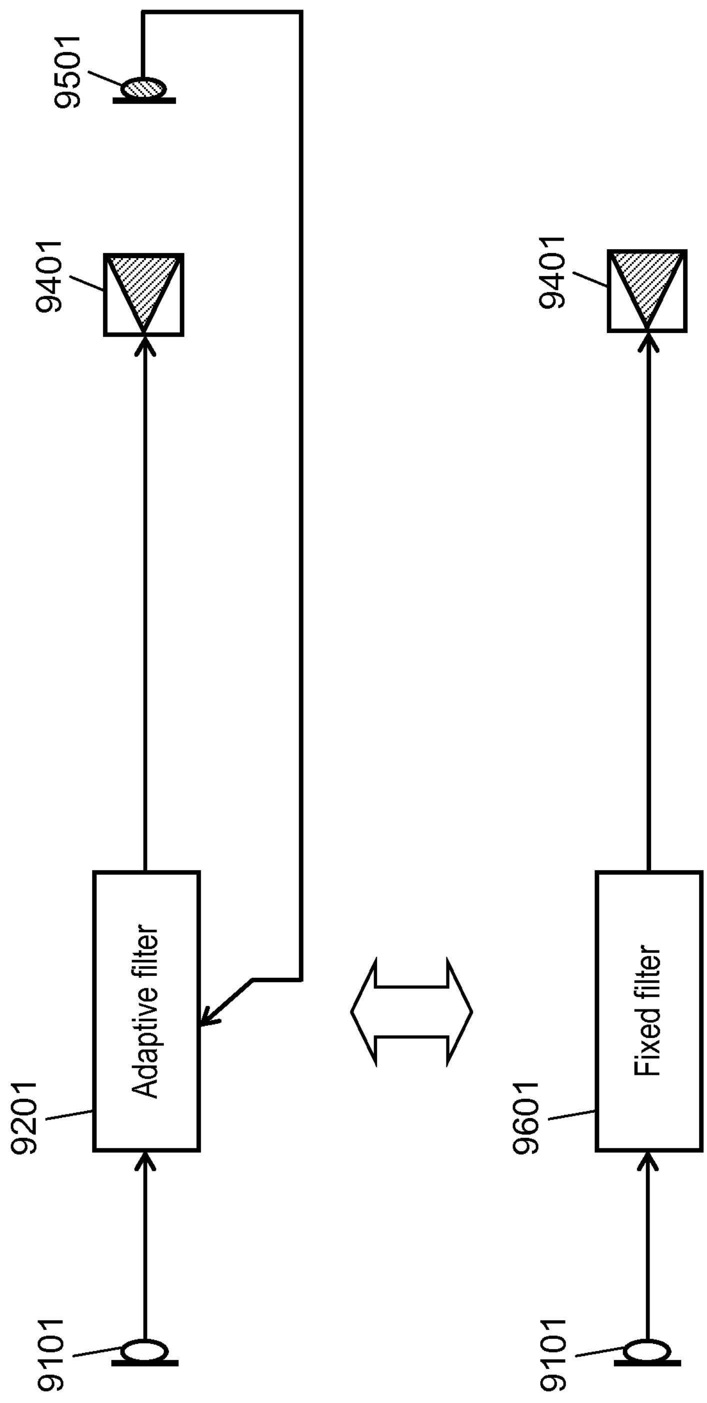
FIG. 9 is a block diagram showing a control method of a conventional noise reduction device.

Here, description is provided of a method of determining the presence or absence of obstacles by finding a change in the acoustic characteristic of the signal sound produced from control speaker 41 and detected by error microphone 51. FIGS. 8A and 8B show frequency characteristics of white noises produced from the control speaker and detected by the error microphone. In FIGS. 8A and 8B, the abscissa and the ordinate represent sound pressure level (dB) and frequency (Hz) in logarithmic representation, respectively. The solid lines in FIGS. 8A and 8B show frequency characteristics when error microphone 51 is not covered, and the dotted lines show frequency characteristics when error microphone 51 is covered. As the dotted line in FIG. 8A shows the frequency characteristic when error microphone 51 is covered with a hand, it is known that the sound pressure level decreases in a region of high frequency as compared with the characteristic with error microphone 51 not covered, and the sound pressure increases in a certain range due to the influence of the sound being muffled. The dotted line in FIG. 8B shows the frequency characteristic when error microphone 51 is covered with a pillow. It is known that the sound pressure level decreases in a wide range from the mid frequency region to the high frequency region when compared with the characteristic with error microphone 51 not covered. This is considered to be attributable to the pillow made of a soft material that absorbs efficiently the high frequency component of the signal. As is obvious from the above example, the covering object causes a substantial change in the characteristic, especially in the region of high frequency. It thus becomes possible to detect the covering object by monitoring changes in the frequency characteristic with time by means of the individual error microphones 51. It is also obvious that similar method of detection is applicable to noise-detecting microphones 11 to 13 besides error microphones 51.

Although what has been described above is the example of producing the signal sound from control speaker 41, it is also possible to monitor changes of background noise inside the aircraft instead of the changes in the frequency characteristic of the signal sound caused by an obstacle. In this disclosed system of device 1, a plurality of error microphones and noise-detecting microphones are disposed around the seat, and it is therefore very unlikely that any obstacle can causes the frequency characteristics monitored by all of the microphones to change at the same time. A criterion of determination can be included for this reason so that any changes in the frequency characteristics of the monitored signals, if occur simultaneously on more than half of the plurality of microphones, is judged as a change in frequency characteristic of the background noise of the aircraft instead of an emerging obstacle, thereby improving the detecting accuracy.

In FIG. 4, the signals output from obstacle detectors 11*s* to 13*s* and 51*s* are transmitted separately from the signals output from noise-detecting microphones 11 to 13 and error microphone 51. However, the signals from noise-detecting microphones 11 to 13 may be superposed upon the signals from obstacle detectors 11*s* to 13*s* when transmitting them, as a method adoptable to integrate these transmission lines.

As a basic operation to cope with obstacles, "Obstruction Pattern Cross-Reference Table" (Filter Coefficient Control Table) is prepared and stored beforehand in filter coefficient memory 81 (filter coefficient storage unit) provided within filter coefficient updating unit 80, wherein filter coefficients of the individual noise-detecting microphones 11 to 13 are allocated according to data of the noises detected by these noise-detecting microphones 11 to 13 under the above-described condition of predetermined noise corresponding to obstruction patterns classified based on presence and absence of the obstacles to noise-detecting microphones 11 to 13. In the example of this device 1 comprising three noise-detecting microphones 11 to 13, there exist eight (8) obstruction patterns.

FIG. 6 shows an example of the obstruction pattern cross-reference table (cross-reference storage unit) stored in filter coefficient memory 81 of device 1. This table includes filter coefficients $F_{11}$, $F_{12}$, $F_{21}$ - - - and $F_{73}$ for fixed filters 21 to 23 when noise reduction is executed according to the data detected by noise-detecting microphones 11 to 13 and error microphone 51 corresponding to obstruction patterns 1 through 8 under the predetermined noise condition. The filter coefficients to be set to individual fixed filters 21 to 23 are allocated to the obstruction patterns 1 through 8. For example, $F_{11}$ denotes a filter coefficient of fixed filter 21 corresponding to obstruction pattern 1, and $F_{73}$ denotes a filter coefficient of fixed filter 23 corresponding to obstruction pattern 7.

The basic operation of device 1 related to the updating process of filter coefficients has already been described.

Fixed filters 21 to 23 (FIG. 4) operate with fixed filter coefficients, which are read from filter coefficient memory 81 and set to the individual fixed filters, and these filter coefficients in filter coefficient memory 81 are updated periodically in a manner to minimize the output of error microphone 51. Calculation of the filter coefficients is executed in off-line mode, in that the noise signals detected by noise-detecting microphones 11 to 13 and the residual sound signal detected by error microphone 51 are stored (or recorded) in signal storage unit 60 and the filter coefficients are calculated by taking a predetermined time. However, these basic operations are limited depending on the presence or absence of obstacles to noise-detecting microphones 11 to 13 and error microphone 51. Description provided next pertains to an operation when device 1 detects an obstacle.

At the time of updating the filter coefficients, filter coefficient calculation unit 70 checks a result of detection of any obstacle to noise-detecting microphones 11 to 13 and error microphone 51 according to detection data received from obstacle detectors 11*s* to -13*s* and 51*s*. If an obstacle appears to exist at error microphone 51, it verifies presence or absence of the obstacle according to the detection data of noise-detecting microphones 11 to 13, but the filter coefficients are not updated when there is no sign of changes in the obstruction patterns of noise-detecting microphones 11 to 13. Or, when there is a change in the obstruction patterns of noise-detecting microphones 11 to 13, filter coefficient calculation unit 70 reads out the filter coefficients of the individual noise-detecting microphones corresponding to the related obstruction pattern by referring to the obstruction pattern stored in filter coefficient memory 81, and updates the filter coefficients by sending a command of update to filter coefficient updating unit 80. If error microphone 51 is covered (when there is an obstacle) and no corresponding obstruction pattern is available, then filter coefficient calculation unit 70 stops the operation of noise reduction.

When there is no obstacle to error microphone 51, on the other hand, filter coefficient calculation unit 70 calculates a new filter coefficient in off-line mode, and compares a difference between a residual sound signal calculated by using the new filter coefficient and another residual sound signal calculated according to the filter coefficient before being updated. Filter coefficient calculation unit 70 then updates the filter coefficient stored in filter coefficient memory when an error based on the new filter coefficient is smaller than the error prior to the update.

In a process to deal with an obstacle that prevents the detection partially, there is a method available such as locating a position of the obstacle by measuring a distance of the obstacle from the noise-detecting microphone with infrared rays, and adding a correction to the obstruction pattern cross-reference table (filter coefficient control table).

Figure 7:
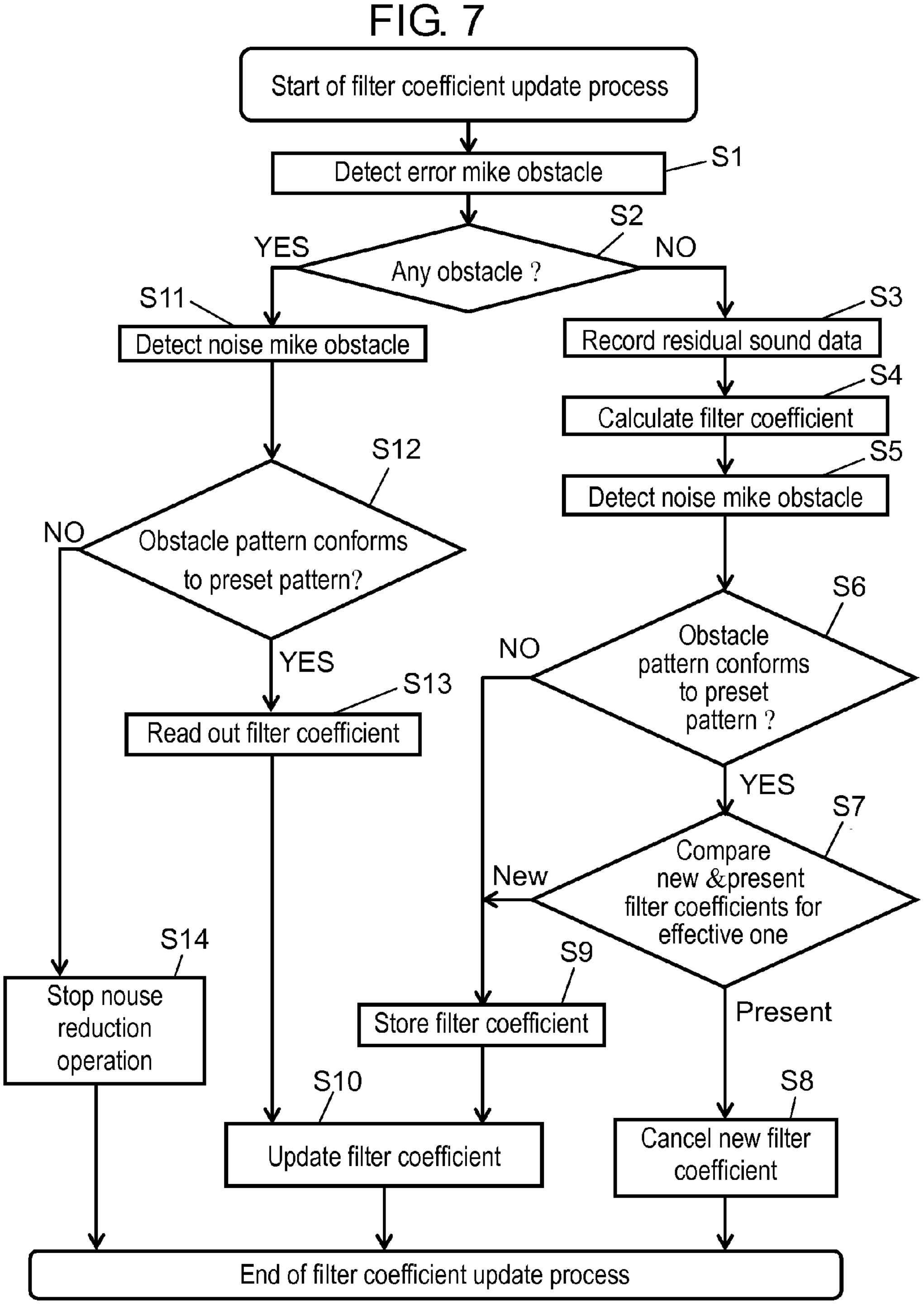
FIG. 7 is a flow chart showing operation processes of updating a filter coefficient of the noise reduction device according to the first exemplary embodiment of the invention.

FIG. 7 is a flow chart showing operation processes of updating the filter coefficients of this device 1. As shown in FIG. 7, the update process of the filter coefficients begins as needed at the timing of periodic update of the filter coefficients or when an obstacle is detected, for example. In step S1, filter coefficient calculation unit 70 starts detecting an obstacle to the error microphone by checking detection data of obstacle detector 51*s* placed in the vicinity of error microphone 51.

In step S2, determination is made of presence or absence of an obstacle to error microphone 51 according to obstacle detection data received from obstacle detector 51*s* by referring to the criteria provided beforehand. The process goes on to step S3 when determined of no obstacle to error microphone 51.

In step S3, data such as residual sound data of error microphone 51 and other noise data are stored (recorded) in signal storage unit 60 for a predetermined time period.

In step S4, optimum filter coefficient is calculated in filter coefficient calculation unit 70 according to the noise data of the predetermined time period stored in signal storage unit 60.

In the next step S5, detection is carried out of an obstacle to noise-detecting microphones 11 to 13 according to obstacle detection data received from obstacle detectors 11*s* to 13*s*. In step S6, a result of obstacle detection is compared with obstruction patterns by referring to the obstruction pattern cross-reference table (FIG. 6) stored beforehand in filter coefficient updating unit 80 to determine based on the criteria provided beforehand as to whether the result conforms to any of the predetermined patterns tabulated in the obstruction pattern cross-reference table. The process goes to step S7 when the result of determination is conformity to one of the predetermined patterns (when it is "YES" in step S6).

In step S7, comparison is made of the effect of noise reduction between the new filter coefficient calculated in step S4 and the existing filter coefficient. The new filter coefficient is cancelled if the existing filter coefficient has a higher effect (step S8), and the filter coefficient updating process ends. When the new filter coefficient has a higher effect, on the other hand, the filter coefficient of the applicable fixed filters 21 to 23 is updated (step S10) after the new filter coefficient is stored in filter coefficient memory 81 of filter coefficient updating unit 80 (step S9), and the filter coefficient updating process ends. In another case if the result of determination in step S6 shows no conformity to any of the prescribed patterns (including "NO" in step S6), the process goes to step S9, and the new filter coefficient is stored as a new pattern in filter coefficient memory 81 of filter coefficient updating unit 80.

In the determination in step S2 as to the presence or absence of an obstacle to error microphone 51, if the result shows presence of an obstacle to error microphone 51, the process goes to step S11, wherein detection is carried out of any obstacle to noise-detecting microphones 11 to 13 according to obstacle detection data received from obstacle detectors 11*s* to 13*s*. In step S12, a result of obstacle detection is compared with obstruction patterns by referring to the obstruction pattern cross-reference table to determine as to whether the result conforms to any of the predetermined patterns tabulated in the obstruction pattern cross-reference table. The process then goes to step S13 when the result of determination is conformity to one of the predetermined patterns (when it is "YES" in step S12).

Afterwards, the filter coefficient is read from the obstruction pattern cross-reference table in step S13, the filter coefficient of the applicable fixed filters 21 to 23 is updated (step S10), and the filter coefficient updating process ends.

On the other hand, when the result of determination in step S12 shows no conformity to any of the prescribed patterns (including "NO" in step S12), the process goes to step S14, wherein the operation of noise reduction is terminated, and the filter coefficient updating process is ended.

According to the exemplary embodiment of this invention, as described above, noise reduction device 1 is provided with obstacle detectors near noise-detecting microphones 11 to 13 and error microphone 51, stores a noise control condition when there is no obstacle, and updates filter coefficients of fixed filters 21 to 23 in control filter unit 90 by using noise control data, thereby making it capable of suppressing increase of the noise attributed to at least an inappropriate filter coefficient updated during presence of any obstacles. The invention can thus provide the noise reduction device of high quality and useful for application to an aircraft, a railcar and the like.

In the above exemplary embodiment, although description has been provided of the method of suspending updating process of the coefficients by prohibiting recording of the noise data, there are also other methods available to suspend updating of the coefficients. Some of the examples include a method of suspending update of the coefficients while continuing the recording, a method of assigning a "zero" weight when updating of the coefficients, as well as other suitable methods, as are obviously known.

With regard to the method of detecting obstacles, many means are available besides the method of detecting signal sound, such as a pressure sensor, infrared sensor, gravimetric sensor, camera and the like so long as they are effective for detection of obstacles.

The invention claimed is:

1. A noise reduction device comprising:

a noise controller unit for generating a control sound signal to cancel out a noise;

a control sound output unit for outputting a control sound according to the control sound signal from the noise controller unit;

a residual sound detector for detecting a residual sound by superimposing the control sound on the noise; and an obstacle detector for detecting an obstacle having potential for influencing detecting performance of the residual sound detector, wherein the noise controller unit generates the control sound signal according to data from the residual sound detector and the obstacle detector, and wherein the noise controller unit comprises:

a control filter unit for outputting a control signal by using a fixed filter coefficient set in advance;

a signal storage unit for storing a residual sound signal detected by the residual sound detector;

a filter coefficient calculation unit for calculating a filter coefficient by using the residual sound signal stored in the signal storage unit; and a filter coefficient updating unit for updating the fixed filter coefficient set in the control filter unit to the filter coefficient calculated by the filter coefficient calculation unit at a predetermined timing.

2. The noise reduction device of claim 1 having a function of prohibiting storage of the residual sound signal in the signal storage unit while the obstacle detector is detecting an obstacle.

3. The noise reduction device of claim 1, wherein the obstacle detector determines presence or absence of an obstacle according to a change in acoustic characteristic of a signal sound detected by the residual sound detector.

4. The noise reduction device of claim 1, wherein the obstacle detector comprises one of an infrared sensor, a pressure sensor, a gravimetric sensor and a camera.

5. A noise reduction device comprising:

a noise detector for detecting a noise supplied from at least one noise source;

a noise controller unit for generating a control sound signal to cancel out the noise detected by the noise detector;

a control sound output unit for outputting a control sound according to the control sound signal from the noise controller unit;

a residual sound detector for detecting a residual sound by superimposing the control sound on the noise supplied from the noise source; and an obstacle detector for detecting an obstacle having potential for influencing detecting performance of at least one of the noise detector and the residual sound detector, wherein the noise controller unit generates the control sound signal according to data from the noise detector, the residual sound detector and the obstacle detector, and wherein the noise controller unit comprises:

a control filter unit for outputting a control signal by using a fixed filter coefficient set in advance;

a signal storage unit for storing a noise signal detected by the noise detector and a residual sound signal detected by the residual sound detector;

a filter coefficient calculation unit for calculating a filter coefficient by using the noise signal and the residual sound signal stored in the signal storage unit; and a filter coefficient updating unit for updating the fixed filter coefficient set in the control filter unit to the filter coefficient calculated by the filter coefficient calculation unit at a predetermined timing.

6. The noise reduction device of claim 4 having a function of prohibiting storage of the residual sound signal in the signal storage unit while the obstacle detector is detecting an obstacle to the residual sound detector.

7. A noise reduction device comprising:

a noise detector for detecting a noise supplied from at least one noise source;

a noise controller unit for generating a control sound signal to cancel out the noise detected by the noise detector;

a control sound output unit for outputting a control sound according to the control sound signal from the noise controller unit;

a residual sound detector for detecting a residual sound by superimposing the control sound on the noise supplied from the noise source; and an obstacle detector for detecting an obstacle having potential for influencing detecting performance of at least one of the noise detector and the residual sound detector, wherein the noise controller unit generates the control sound signal according to data from the noise detector, the residual sound detector and the obstacle detector, wherein the noise controller unit comprises:

a control filter unit for outputting a control signal by using a fixed filter coefficient set in advance;

a signal storage unit for storing a noise signal detected by the noise detector and a residual sound signal detected by the residual sound detector;

a filter coefficient calculation unit for calculating a filter coefficient by using the noise signal and the residual sound signal stored in the signal storage unit;

a filter coefficient storage unit for storing the filter coefficient calculated by the filter coefficient calculation unit; and a filter coefficient updating unit for updating the fixed filter coefficient set in the control filter unit to one of the filter coefficient calculated by the filter coefficient calculation unit and the filter coefficient stored in the filter coefficient storage unit at a predetermined timing.

8. The noise reduction device of claim 7 having a function of prohibiting storage of the noise signal and the residual sound signal in the signal storage unit while the obstacle detector is detecting an obstacle to the residual sound detector.

9. The noise reduction device of claim 7 further comprising a cross-reference storage unit for storing the filter coefficient calculated by the filter coefficient calculation unit and obstacle detection data detected by the obstacle detector when the noise signal and the residual sound signal used for calculation of the filter coefficient are stored in a manner to correspond with each other, wherein the filter coefficient corresponding to the obstacle detection data of the noise detector detected by the obstacle detector is read from the cross-reference storage unit and set to the control filter unit while the obstacle detector is detecting an obstacle to the residual sound detector.

* * * * *